United States Patent [19]
Levine

[11] Patent Number: 5,968,081
[45] Date of Patent: Oct. 19, 1999

[54] SYSTEM AND METHOD FOR PROVIDING IMPROVED FALLBACK RESPONSE IN A DUAL-CHAMBER CARDIAC PACEMAKER

[75] Inventor: Paul A. Levine, Newhall, Calif.

[73] Assignee: Pacesetter, Inc., Sylmar, Calif.

[21] Appl. No.: 08/856,435

[22] Filed: May 14, 1997

Related U.S. Application Data

[60] Provisional application No. 60/017,922, May 15, 1996.

[51] Int. Cl.⁶ ..................................................... A61N 1/36
[52] U.S. Cl. .................................................................. 607/9
[58] Field of Search ................................. 607/9, 14, 15, 607/17, 25

[56] References Cited

U.S. PATENT DOCUMENTS

| | | |
|---|---|---|
| 4,485,818 | 12/1984 | Leckrone et al. . |
| 4,554,920 | 11/1985 | Baker, Jr. et al. ........................... 607/9 |
| 4,624,260 | 11/1986 | Baker et al. . |
| 4,712,555 | 12/1987 | Thornander et al. . |
| 4,712,556 | 12/1987 | Baker, Jr. ..................................... 607/9 |
| 4,940,052 | 7/1990 | Mann et al. . |
| 4,944,928 | 7/1990 | Sholder . |
| 5,085,215 | 2/1992 | Nappholz et al. ........................... 607/9 |
| 5,161,527 | 11/1992 | Nappholz et al. ........................... 607/9 |
| 5,476,483 | 12/1995 | Bornzin et al. . |
| 5,549,649 | 8/1996 | Florio et al. . |
| 5,584,867 | 12/1996 | Limousin et al. . |

*Primary Examiner*—Jeffrey R. Jastrzab

[57] ABSTRACT

An implantable dual-chamber pacemaker programmed to operate primarily in a P-wave tracking mode, where the pacemaker switches to a fallback response at a threshold rate higher than a maximum tracking rate of the pacemaker. When the fallback response is initiated the ventricular pacing rate is progressively reduced to a fallback rate. The pacemaker exits the fallback response when programmable fallback exit criteria are met.

54 Claims, 5 Drawing Sheets

SYSTEM AND METHOD FOR PROVIDING IMPROVED FALLBACK RESPONSE IN A DUAL-CHAMBER CARDIAC PACEMAKER

This application claims the benefit of U.S. Provisional Application No. 60/017,922, May 15, 1996.

FIELD OF THE INVENTION

The present invention relates generally to cardiac pacemakers, and more particularly to a rate-responsive, dual-chamber pacemaker programmed to operate in a P-wave tracking mode, where the pacemaker initiates a fallback response at a threshold rate higher than a maximum tracking rate of the pacemaker.

BACKGROUND OF THE INVENTION

Essentially, the heart is a pump which pumps blood throughout the body. It consists of four chambers—two atria and two ventricles. In order for the heart to efficiently perform its function as a pump, the atrial muscles and ventricular muscles should contract in a proper sequence and in a timed relationship.

In a given cardiac cycle (corresponding to one "beat" of the heart), the two atria contract, forcing the blood therein into the ventricles. A short time later, the two ventricles contract, forcing the blood therein to the lungs (from the right ventricle) or through the body (from the left ventricle). Meanwhile, blood from the body fills the right atrium and blood from the lungs fills the left atrium, waiting for the next cycle to begin. A typical healthy adult heart may beat at a rate of 60–80 beats per minute (bpm) while at rest, and may increase its rate to 140–180 bpm when the adult is engaging in strenuous physical exercise, or undergoing other physiologic stress.

The healthy heart controls its rhythm from its sino-atrial (SA) node, located in the upper portion of the right atrium. The SA node generates an electrical impulse at a rate commonly referred to as the "sinus" or "intrinsic" rate. This impulse is delivered to the atrial tissue when the atria are to contract and, after a suitable delay (on the order of 40–80 milliseconds), propagates to the ventricular tissue when the ventricles are to contract.

The detectable electrical signal which causes the atria to contract, is referred to as a P-wave, while the detectable electrical signal which causes the ventricles to contract is referred to as a QRS complex often abbreviates as an R-wave. The R-wave is much larger than the P-wave, principally because the ventricular muscle tissue is much more massive than the atrial muscle tissue. The atrial muscle tissue need only produce a contraction sufficient to move the blood a very short distance—from the respective atrium to its corresponding ventricle. The ventricular muscle tissue, on the other hand, must produce a contraction sufficient to push the blood over a long distance (e.g., through the complete circulatory system of the entire body).

The electrical signal or wave most commonly detectable within a cardiac cycle, is the T-wave (which represents the depolarization of the ventricular muscle tissue).

It is the function of a pacemaker to provide electrical stimulation pulses to the appropriate chamber(s) of the heart (atria or ventricles) in the event the heart is unable to beat on its own (i.e., in the event either the SA node fails to generate its own natural stimulation pulses at an appropriate sinus rate, or in the event such natural stimulation pulses do not effectively propagate to the appropriate cardiac tissue). Most modern pacemakers accomplish this function by operating in a "demand" mode where stimulation pulses from the pacemaker are provided to the heart only when it is not beating on its own, as sensed by monitoring the appropriate chamber of the heart for the occurrence of a P-wave or an R-wave. If a P-wave or an R-wave is not sensed within a prescribed period of time (referred to as the "escape interval"), then a stimulation pulse is generated at the conclusion of this prescribed period of time and delivered to the appropriate heart chamber via a pacemaker lead.

Modern programmable pacemakers are generally of two types: (1) single chamber pacemakers, and (2) dual-chamber pacemakers. In a single chamber pacemaker, the pacemaker provides stimulation pulses to, and senses cardiac activity within, a single chamber of the heart (e.g., either the right ventricle or the right atrium). In a dual-chamber pacemaker, the pacemaker provides stimulation pulses to, and senses cardiac activity within, two chambers of the heart (e.g., both the right atrium and the right ventricle). The left atrium and left ventricle can also be paced, provided that suitable electrical contacts are made therewith.

In general, both single and dual-chamber pacemakers are classified by type according to a three letter code. In this code, the first letter identifies the chamber of the heart that is paced (i.e., the chamber where a stimulation pulse is delivered)—with a "V" indicating the ventricle, an "A" indicating the atrium, and a "D" indicating dual or both the atrium and ventricle. The second letter of the code identifies the chamber where cardiac activity is sensed, using the same letters to identify the atrium or ventricle or both, and where an "O" indicates that no sensing takes place.

The third letter of the code identifies the action or response that is taken by the pacemaker. In general, two types of action or responses are recognized: (1) an Inhibiting ("I") response, where a stimulation pulse is delivered to the designated chamber after a set period of time unless cardiac activity is sensed during that time, in which case the stimulation pulse is inhibited; (2) a Trigger ("T") response, where a stimulation pulse is delivered to the designated chamber of the heart a prescribed period after a sensed event. Both of the abovedescribed responses may be combined resulting in a Dual ("D") response, where both the Inhibiting mode and Trigger mode are evoked, inhibiting in one chamber of the heart and triggering in the other.

A fourth letter, "R", is sometimes added to the code to signify that the particular mode identified by the three letter code is rate-responsive, where the pacing rate may be adjusted automatically by the pacemaker based on one or more physiological factors, such as blood oxygen level or the patient's activity level.

Thus, for example, a DVI pacemaker is a pacemaker that paces in both chambers of the heart, but only senses in the ventricle, and that operates by inhibiting stimulation pulses when prior ventricular activity is sensed. Because it paces in two chambers, it is considered a dual-chamber pacemaker. A VVI pacemaker, on the other hand, is a pacemaker that paces only in the ventricle. Because only one chamber is involved, it is classified as a single chamber pacemaker. Most dual-chamber pacemakers can also be programmed to operate in a single chamber mode.

Much has been written and described about the various types of pacemakers and the advantages and disadvantages of each. For example, commonly assigned U.S. Pat. No. 4,712,555 of Thornander et al. presents background information about pacemakers and the manner in which they interface with a patient's heart. This patent is hereby incorporated by reference in its entirety.

One of the most versatile programmable pacemakers available today is the DDDR pacemaker. This pacemaker represents a fully automatic pacemaker which is capable of sensing and pacing in both the atrium and the ventricle, and is also capable of adjusting the pacing rate based on one or more factors independent of the intrinsic electrical depolarization signals generated by the heart, but indicative of a need for a faster heart rate—such as the patient's activity level. When functioning properly, the DDDR pacemaker can limit certain drawbacks associated with the use of pacemakers. For example, the DDDR pacemaker can maintain AV synchrony while providing bradycardia support at progressively higher rates based upon physiologic requirements.

In general, DDD pacing has four functional states: (1) P-wave sensing, ventricular pacing (PV); (2) atrial pacing, ventricular pacing (AV); (3) P-wave sensing, R-wave sensing (PR); and (4) atrial pacing, R-wave sensing (AR). Advantageously, for the patient with complete or partial heart block, the PV state of the DDD pacemaker tracks the atrial rate which is set by the heart's SA node, and then paces in the ventricle at a rate that follows this atrial rate. Because the rate set by the SA node represents the rate at which the heart should beat in order to meet the physiologic demands of the body (at least for a heart having a properly functioning SA node) the rate maintained in the ventricle by such a pacemaker is truly physiologic.

Those skilled in the art have long recognized the advantages of using an atrial rate-based (i.e. P-wave tracking) pacemaker. For example, U.S. Pat. No. 4,624,260 to Baker, Jr. et al. discloses a microprocessor-controlled dual-chamber pacemaker having conditional atrial tracking capability. Similarly, U.S. Pat. No. 4,485,818 of Leckrone et al. discloses a microprocessor-based pacemaker which may be programmed to operate in one of a plurality of possible operating modes, including an atrial rate tracking mode.

Unfortunately, in some instances, a given patient may develop fast atrial rhythms which result from a pathologic arrhythmia such as a pathological tachycardia, fibrillation, or flutter. In these cases, a DDD(R) pacemaker may pace the ventricles in response to the sensed atrial arrhythmia up to a programmed maximum tracking rate (MTR). The MTR defines the upper limit for the ventricular rate when the pacemaker is tracking the intrinsic atrial rate (IAR). As a result, the MTR sets the limit above which the ventricles cannot be paced, regardless of the intrinsic atrial rate. Thus, the purpose of the MTR is to prevent rapid ventricular stimulation, which could occur if the intrinsic atrial rate becomes very high and the pacemaker attempts to track intrinsic atrial activity with 1:1 AV synchrony.

Pacemakers also incorporate a programmable parameter known as an atrial refractory period, which is initiated by either a paced or sensed cardiac event. The atrial refractory period, also called a total atrial refractory period (TARP), is made up of two segments. The first segment, known as the AV Delay (AVD), is initiated by a paced or sensed atrial event. The second segment, known as the post ventricular atrial refractory period (PVARP), is initiated by a paced or sensed ventricular event. The TARP (measured in milliseconds (ms)) is inversely proportional to the highest sensed atrial rate. Thus, the highest sensed atrial rate in beats per minute (bpm) is 60,000/TARP in milliseconds. In some DDD pacemakers the MTR equals the highest sensed atrial rate. When the intrinsic atrial rate continues to increase above the MTR, every other P-wave coincides with the TARP. P-waves occurring during the TARP are not sensed and thus are not tracked. Because the pacemaker responds to every other P-wave, the paced ventricular rate plummets to a value which is one half of the intrinsic atrial rate. This is called a fixed block or a 2:1 block upper rate response.

Other pacemakers have an independently programmable MTR interval (MTRI). It is longer than the TARP hence the MTR is below the highest sensed atrial rate. When the intrinsic atrial rate exceeds the MTR but is below the highest sensed atrial rate, each P-wave will be sensed but the timing circuit of the pacemaker will not allow the paced ventricular rate to exceed the programmable MTR. This results in a progressive lengthening of the P-sensed to V-paced interval until a P-wave coincides with the TARP. The P-wave occurring during the TARP is not sensed and hence is not tracked. This results in a pause followed by a repeat of the previous series of PV complexes. This is called pacemaker Wenckebach upper rate behavior.

In both of the above examples atrial events occurring during the TARP are not tracked by the pacemaker for the purpose of pacing the ventricles because pacing the ventricles at an intrinsic atrial rate exceeding the MTR may be dangerous. Instead, as described above, only atrial events occurring outside the TARP are tracked in order to maintain the ventricular pacing rate at a safe level.

Advancements in pacemaker technology have been driven by a desire to approximate true physiological cardiac activity through pacing. In recent years many developments in pacemaker technology, such as rate-responsive pacing, have enabled pacemakers to better emulate some of the functions of the healthy heart. In addition, a number of the developments have improved the comfort of a patient with an implanted pacemaker, especially during the time when the patient's intrinsic atrial rate is high. One upper rate response is known as "fallback behavior." The fallback behavior response differs from other upper rate responses, such as mode-switching, in that the fallback behavior minimizes the patient's discomfort during high intrinsic atrial rate operation by reducing a high ventricular pacing rate to a lower rate in a gradual rather than a sudden manner. The fallback behavior is particularly advantageous for patients for whom sudden drops in the ventricular pacing rate may cause bothersome palpitations or other symptoms.

Another common upper rate response is mode switching. Mode switching is an upper rate response whereby when the intrinsic atrial rate exceeds the MTR the pacemaker automatically switches the pacemaker's mode of operation, for example from a P-wave tracking mode to a non-P-wave tracking mode. Mode switching is described in greater detail in commonly assigned U.S. Pat. No. 5,549,649, issued Aug. 27, 1996, entitled "Programmable Pacemaker Including an Atrial Rate Filter for Deriving a Filtered Atrial Rate Used for Switching Pacing Modes," which is hereby incorporated by reference in its entirety.

As an upper rate response, the fallback behavior is usually invoked when the intrinsic atrial rate exceeds the MTR. Thus, in most previously known pacemakers in which fallback was present, the MTR is also a fallback initiating rate (FIR). Since pacing the ventricles at a rate exceeding the MTR may be dangerous, when the intrinsic atrial rate exceeds the MTR the typical fallback behavior response causes the pacemaker to gradually reduce the ventricular pacing rate to a pre-set programmable fallback rate (FR). The fallback rate is usually a fairly low value, closer to a base rate (BR) than to the MTR. The base rate is typically the minimum rate at which the ventricles and the atria may be paced. The reduction of the ventricular pacing rate to the fallback rate is usually performed by progressively extending the ventricular pacing interval of each cardiac cycle. The pacemaker then paces the ventricles at the fallback rate as long as the intrinsic atrial rate is above the MTR. When the intrinsic atrial rate drops below the MTR the pacemaker sets the ventricular pacing rate equal to the intrinsic atrial rate and resumes 1:1 AV synchronous pacing.

The fallback initiating rate of previously known pacemakers may differ from the MTR but is not typically set above the MTR (even though intrinsic atrial rate exceeding the MTR may be monitored). This arrangement may be problematic for patients whose normal heart rates may slightly exceed the MTR for periods of time. Patients who engage in physical activity, young patients, and patients in an excited emotional state may all exhibit temporary increases in intrinsic atrial rate—where the intrinsic atrial rate exceeds the MTR, but is not indicative of a pathological arrhythmia. As a result, an active patient whose intrinsic atrial rate slightly exceeds the MTR during physical activity or an excited emotional state would be paced at the lower fallback rate which, if insufficient for the activity level, would be inappropriate. Thus, most previously known pacemakers equipped with the fallback behavior response do not distinguish between a high intrinsic atrial rate due to physical activity or an excited emotional state, and a high intrinsic atrial rate due to a pathological arrhythmia. As a result, most previously known pacemakers initiate the fallback behavior response even if the patient is experiencing a temporary high physiologic intrinsic atrial rate which is non-pathologic.

Another drawback of the previously known fallback behavior response is that during fallback operation, the fallback behavior response causes the pacemaker to switch from pacing at the fallback rate to pacing at the intrinsic atrial rate as soon as the intrinsic atrial rate drops below the MTR. This approach is problematic because if the intrinsic atrial rate drops below the MTR for a few cycles and then increases to a rate above the MTR, the patient will experience an increase and then a drop in the ventricular pacing rate over several cycles as the pacemaker attempts to leave and re-enter the fallback behavior. This may occur when a patient is engaging in sporadic physical activity. For example, if a patient is jogging, the patient's intrinsic atrial rate may exceed the MTR while the patient is moving, but may drop below the MTR if the patient pauses to rest. As a result, the patient will experience an increase in the pacing rate when the patient stops moving (since the intrinsic atrial rate temporarily drops below the MTR and the fallback behavior is exited), and a decrease in the pacing rate when the patient once again begins to jog (since the intrinsic atrial rate exceeds the MTR, and the fallback behavior is initiated).

Finally, an apparently low intrinsic atrial rate during a number cardiac cycles may cause the pacemaker to exit the fallback behavior under the assumption that the intrinsic atrial rate dropped below the MTR for more than a few cycles. As a result, the patient may be exposed to a frequent variation of pacing rates as the pacemaker exits and re-enters the fallback behavior with the attendant loss of AV synchrony when fallback behavior is engaged.

Thus it would be desirable to provide a pacemaker capable of initiating the fallback behavior at a programmable rate higher than the MTR, when the patient is likely to be experiencing a pathological arrhythmia. It would also be desirable to provide a pacemaker which would only exit the fallback behavior if programmable fallback exit criteria were met.

SUMMARY OF THE INVENTION

The disadvantages and limitations discussed above are overcome by the present invention. In accordance with the present invention, an implantable dual-chamber pacemaker programmed to operate primarily in a P-wave tracking mode is provided, where the pacemaker switches to a fallback response at a threshold rate higher than a maximum tracking rate of the pacemaker. During the fallback response the ventricular pacing rate is gradually reduced to a fallback rate. The pacemaker of the present invention exits the fallback response when programmable fallback exit criteria are met.

The pacemaker of the present invention includes a control system for controlling the operation of the pacemaker, a set of leads for receiving atrial and ventricular signals and for delivering atrial and ventricular stimulation pulses, a set of amplifiers for amplifying the atrial and ventricular signals, and pulse generators for generating atrial and ventricular stimulation pulses. In addition, the pacemaker includes memory for storing operational parameters for the control system and for storing data acquired by the control system for later retrieval by the medical practitioner using an external programmer. The pacemaker also includes a telemetry circuit for communicating with the external programmer.

The pacemaker of the present invention continually monitors the intrinsic atrial rate when it exceeds the MTR by sensing all atrial events, even those falling into the refractory periods. A system capable of sensing atrial events occurring during the refractory periods is described in commonly assigned U.S. Pat. No. 4,944,928 of Sholder, which is hereby incorporated by reference in its entirety. As a result, the pacemaker of the present invention is capable of initiating the fallback response at a fallback initiating rate higher than the MTR. The fallback initiating rate may be programmed by the medical practitioner, but is preferably set at 30–50 bpm above the MTR, because during an arrhythmia the patient's intrinsic atrial rate will most likely exceed the MTR by 100 or more bpm (the actual number depends on the rhythm and programmed MTR), while during strenuous activity, the patient's intrinsic atrial rate is unlikely to exceed the MTR by more than 20–30 bpm. Thus, if the intrinsic atrial rate exceeds the MTR but is below the fallback initiating rate, the intrinsic atrial rate may be considered non-pathologic and the fallback response is not initiated. This approach is advantageous because it prevents fallback from occurring when the high intrinsic atrial rate is due to natural causes such as physical activity or an excited emotional state, and initiates the fallback response only when the intrinsic atrial rate is most likely pathologic (i.e., when the intrinsic atrial rate exceeds the fallback initiating rate). During the period when the intrinsic atrial rate is between the MTR and the fallback initiating rate, the ventricles are paced at the MTR to provide the required elevated cardiac output.

The fallback response is preferably implemented by progressively decreasing a ventricular pacing rate (VPR) during each cardiac cycle by an incremental amount. This may be accomplished by increasing a ventricular pacing interval (VPI) by a programmable fallback step (measured in ms) during each cardiac cycle. Assuming a ventricular pacing interval of 375 ms when the ventricular pacing rate is at 160 bpm, a 10 ms fallback step increase in the ventricular pacing interval during a cardiac cycle corresponds to a drop of approximately 3 bpm in the ventricular pacing rate during that cycle. The progressive reduction of the ventricular pacing rate continues until the ventricular pacing rate reaches the fallback rate, or until the fallback response is exited, whichever occurs first. The medical practitioner can increase the time it takes for the ventricular pacing rate to reach the fallback rate by decreasing the value of the fallback step by an appropriate number of ms, or decrease the time it takes for the ventricular pacing rate to reach the fallback rate by increasing the value of the fallback step by an appropriate number of ms.

In addition, the pacemaker of the present invention preferably exits from the fallback response when programmable fallback exit criteria are met. This approach is advantageous because it prevents frequent switching to and from the fallback response if the intrinsic atrial rate drops below the MTR for only a few cycles due to a pause in the patient's physical activity, or due to a dropout (temporary deactivation) in the atrial sense channel (as may occur when a series of therapeutic pulses are delivered). This approach ensures that the intrinsic atrial rate has dropped below the MTR for more than a few cycles before the fallback response is exited. This is accomplished by monitoring the intrinsic atrial rate in accordance with the fallback exit criteria and exiting the fallback response only if the fallback exit criteria have been met. For example, the fallback criteria may require that the intrinsic atrial rate remain below the MTR for 20 contiguous cardiac cycles before the pacemaker exits the fallback response.

The pacemaker of the present invention improves the comfort of a patient by initiating the fallback response at a rate higher than the MTR, thus ensuring that the fallback response is initiated only when a high intrinsic atrial rate is indicative of a pathologic arrhythmia. The pacemaker of the present invention further improves the comfort of a patient by remaining in the fallback response until the intrinsic atrial rate is verified to be at a comfortable level (i.e., when the intrinsic atrial rate meets the fallback exit criteria). In another aspect of this invention, a method for initiating the fallback response mode at a rate higher than the MTR and for exiting the fallback response when fallback exit criteria are met is provided.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which.

DETAILED DESCRIPTION OF THE PREFERRED EMBODIMENTS

Figure 1:
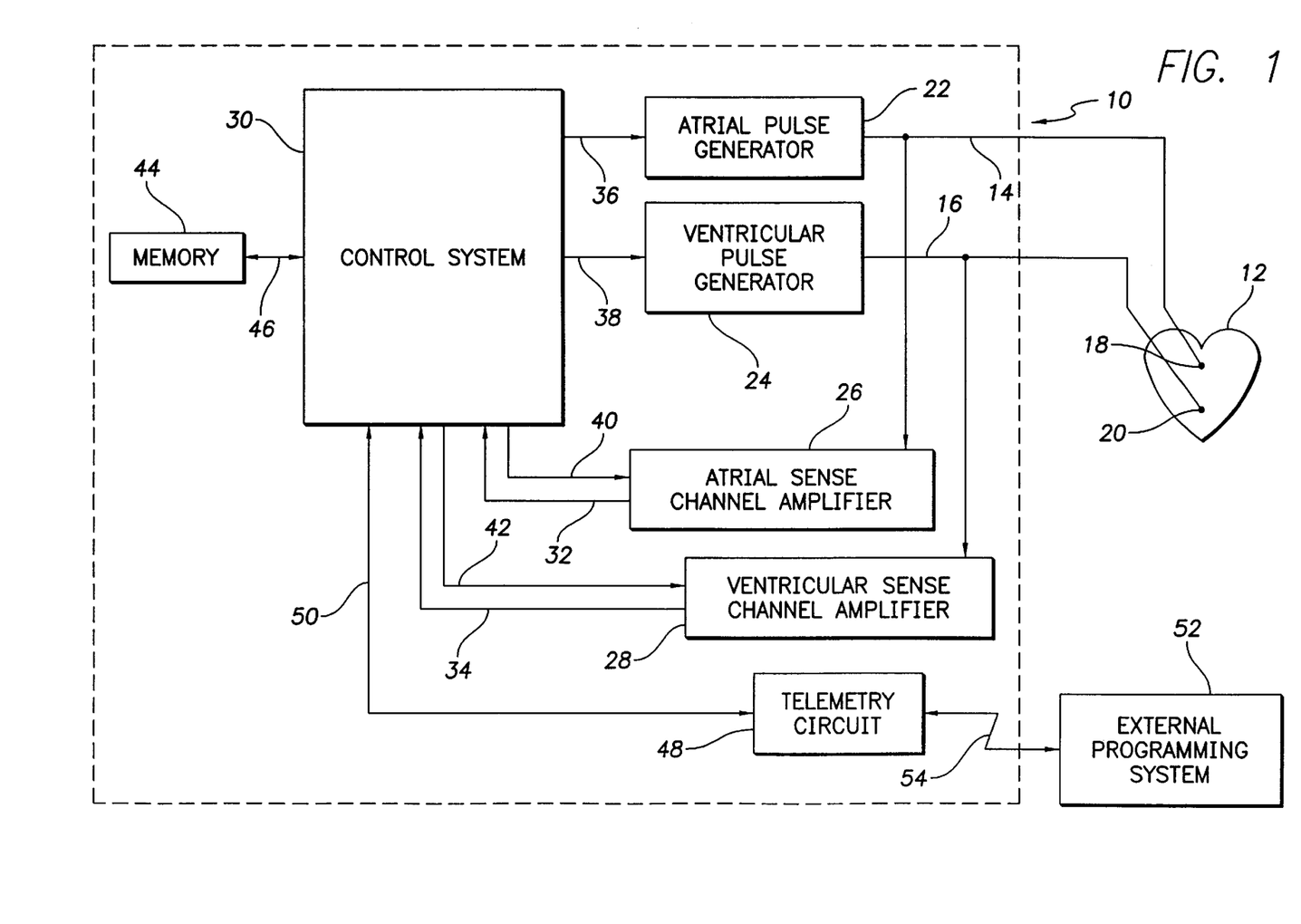
FIG. 1 is a block diagram of a dual-chamber pacemaker in accordance with the principles of the present invention.

A pacemaker 10 in accordance with this invention is shown in FIG. 1. The pacemaker 10 is coupled to a heart 12 by way of leads 14 and 16, the lead 14 having an electrode 18 which is in contact with one of the atria of the heart 12, and the lead 16 having an electrode 20 which is in contact with one of the ventricles. The lead 14 carries stimulating pulses to the electrode 18 from an atrial pulse generator 22, while the lead 16 carries stimulating pulses to the electrode 20 from a ventricular pulse generator 24. In addition, electrical signals from the atria are carried from the electrode 18, through the lead 14 to the input terminal of an atrial sense amplifier 26. Electrical signals from the ventricles are carried from the electrode 20, through the lead 16 to the input terminal of a ventricular sense amplifier 28.

Controlling the dual-chamber pacemaker 10 is a control system 30. The control system 30 is preferably a microprocessor-based system such as the one disclosed in commonly assigned U.S. Pat. No. 4,940,052 of Mann, which is hereby incorporated by reference in its entirety. The control system 30 may also be a state logic-based system such as the one disclosed in above-incorporated U.S. Pat. No. 4,944,298 of Sholder. The control system 30 also includes a real-time clock (not shown) for providing timing for monitoring cardiac events and for timing the application of therapeutic pulses by the pulse generators 22 and 24.

The control system 30 receives the output signals from the atrial amplifier 26 over a signal line 32. Similarly, the control system 30 receives the output signals from the ventricular amplifier 28 over a signal line 34. These output signals are generated each time that an atrial event (e.g., a P-wave) or a ventricular event (e.g., an R-wave) is sensed within the heart 12.

The control system 30 also generates an atrial trigger signal which is sent to the atrial pulse generator 22 over a signal line 36, and a ventricular trigger signal which is sent to the ventricular pulse generator 24 over a signal line 38. These trigger signals are generated each time that a stimulation pulse is to be generated by one of the pulse generators 22 or 24. The atrial stimulation pulse is referred to simply as the "a-pulse," and the ventricular stimulation pulse is referred to as the "V-pulse."

During the time that either an a-pulse or a V-pulse is being delivered to the heart 12, the corresponding atrial amplifier 26 or the ventricular amplifier 28 is typically disabled by way of a blanking signal presented to the appropriate amplifier from the control system 30 over a signal line 40 for the atrial amplifier 26 or a signal line 42 for the ventricular amplifier 28. This blanking action prevents the amplifiers 26 and 28 from becoming saturated with the relatively large stimulation pulses which are present at their input terminals during pacing pulse delivery. This blanking action also prevents residual electrical signals (known as "afterpotentials" or polarization) present in the muscle tissue as a result of the pacemaker stimulation from being interpreted as atrial or ventricular events.

The pacemaker 10 also includes a memory circuit 44 which is coupled to the control system 30 through a suitable data bus 46. The memory circuit 44 allows certain control parameters used by the control system 30 in controlling the operation of the pacemaker 10 to be programmably stored and modified, as required, in order to customize the operation of the pacemaker 10 to suit the needs of a particular patient. In addition, data sensed during the operation of the pacemaker 10 may be stored in the memory circuit 44 for later retrieval and analysis.

A telemetry circuit 48 is further included in the pacemaker 10. The telemetry circuit 48 is connected to the control system 30 by way of a suitable command/data bus 50. The telemetry circuit 48 may be selectively coupled to an external programming device 52 by means of an appropriate communication link 54. The communication link 54 may be any suitable electromagnetic link such as an RF (radio frequency) channel.

Commands may be sent by the medical practitioner to the control system 30 from the external programmer 52 through the communication link 54. Similarly, through this communication link 54 and the external programmer 52, data (either held within the control system 30, as in a data latch, or stored within the memory circuit 44) may be transmitted by the pacemaker 10 to the external programmer 52. In this manner, non-invasive communication may be established with the implanted pacemaker 10 from a remote, non-implanted location.

The operation of the pacemaker 10 is generally controlled by a control program stored in the memory circuit 44 and executed by the control system 30. This control program usually consists of multiple integrated program modules, with each module bearing responsibility for controlling one or more functions of the pacemaker 10. For example, one program module may control the delivery of stimulating pulses to the heart 12, while another module may control the acquisition of atrial and ventricular electrical signals. In effect, each program module is a control program dedicated to a specific function or a set of functions of the pacemaker 10.

The fallback response control program of the present invention, described below in connection with FIG. 5, operates on several rates measured in beats per minute (bpm) and intervals which are measured in milliseconds (ms). An interval in milliseconds is inversely proportional to the rate in beats per minute. The conversion between the interval and the corresponding rate is accomplished by dividing 60,000 by the interval to get the rate, or by dividing 60,000 by the rate to get the interval. For example, if the interval is 300 ms, the corresponding rate is 60,000/300 or 200 bpm.

Before describing the control program in greater detail, it would be helpful to define the terminology of the various rates and intervals used in the operation of the control program. It would also be helpful to describe the relationships between the various rates and intervals used in the operation of the control program.

An intrinsic atrial rate (IAR) is determined by the control system 30 by first measuring the interval in milliseconds between the P-wave sensed during the current cardiac cycle and the P-wave sensed during the previous cardiac cycle, and then dividing 60,000 by the interval to produce the intrinsic atrial rate in beats per minute (bpm). A maximum tracking rate (MTR) is typically the maximum rate at which the pacemaker 10 (FIG. 1) tracks the intrinsic atrial rate when pacing the ventricles. The MTR is programmable by the medical practitioner using the external programmer 52 (FIG. 1). A typical value for the MTR may be 160 bpm. A base rate (BR) is typically the minimum programmed pacing rate for a particular patient. If the intrinsic atrial rate drops below the base rate, the patient is paced at the base rate. The base rate is programmable by the medical practitioner using the external programmer 52 (FIG. 1). A typical value for the base rate may be 70 bpm.

A total atrial refractory period (TARP) is made up of two segments. The first segment, known as the AV delay (AVD), is initiated by a paced atrial event (such as an a-pulse) generated by the atrial pulse generator 22 (FIG. 1), or by a sensed atrial event (such as a P-wave) sensed by the atrial sense channel amplifier 26 (FIG. 1). The second segment, known as the post ventricular atrial refractory period (PVARP), is initiated by a paced ventricular event (such as a V-pulse) generated by the ventricular pulse generator 24 (FIG. 1), or by a sensed ventricular event (such as an R-wave) sensed by the ventricular sense channel amplifier 28 (FIG. 1). The TARP is the sum of the two segments (AVD and PVARP).

When the intrinsic atrial rate exceeds a programmable fallback initiating rate (FIR), which is higher than the MTR, the control system 30 (FIG. 1) causes the pacemaker 10 (FIG. 1) to enter a fallback response. The fallback initiating rate may be programmed by the medical practitioner using the external programmer 52 (FIG. 1).

A ventricular pacing rate (VPR) is the rate at which the ventricles are paced by the pacemaker 10 (FIG. 1). A ventricular pacing interval (VPI) is inversely proportional to the ventricular pacing rate. The pacemaker 10 (FIG. 1) controls the ventricular pacing rate by increasing or decreasing the ventricular pacing interval.

When the pacemaker 10 (FIG. 1) is operating in the demand mode, ventricular pulses are delivered to the heart only when it is not beating on its own. When the intrinsic atrial rate is below the MTR, the ventricular pacing rate is equal to the intrinsic atrial rate. When the intrinsic atrial rate is equal to or above the MTR but below the fallback initiating rate, the ventricular pacing rate is defined by the fixed block or Wenckebach upper rate behavior equal to the MTR. However, when the intrinsic atrial rate is equal to or exceeds the fallback initiating rate, the fallback response is initiated, and the ventricular pacing rate is progressively reduced (preferably during each cardiac cycle) until a fallback rate (FR) is reached. While the intrinsic atrial rate is above the fallback initiating rate, the ventricles are paced at the fallback rate. When the intrinsic atrial rate falls below the fallback initiating rate, the fallback response is exited and the ventricular pacing rate increases from the fallback rate to the intrinsic atrial rate. The fallback rate may be a constant value programmed by the medical practitioner using the external programmer 52 (FIG. 1). For example, a typical fallback rate value may be 90 bpm. Optionally, the fallback rate may be set equal to the base rate. While the base rate is typically a constant value, it may be a variable value responsive to the patient's physical or emotional state. A preferred implementation of the variable base rate is disclosed in commonly assigned U.S. Pat. No. 5,476,483, issued Dec. 19, 1995, entitled "System and Method for Modulating the Base Rate During Sleep for a Rate-Responsive Cardiac Pacemaker," which is hereby incorporated by reference in its entirety.

The reduction of the ventricular pacing rate to the fallback rate is typically accomplished by incrementally increasing the ventricular pacing interval which is inversely proportional to the ventricular pacing rate. When the fallback response is initiated, the ventricular pacing interval is incrementally increased in programmable fallback steps, one step per cardiac cycle. As the ventricular pacing interval increases, the ventricular pacing rate decreases until the fallback rate is reached. The value of the fallback step may be selected by the medical practitioner using the external programmer 52 (FIG. 1). A typical fallback step value may range from 10 ms to 25 ms per cardiac cycle. The number of cardiac cycles necessary for the ventricular pacing rate to reach the fallback rate is inversely proportional to the value of the fallback step.

Figure 2A:
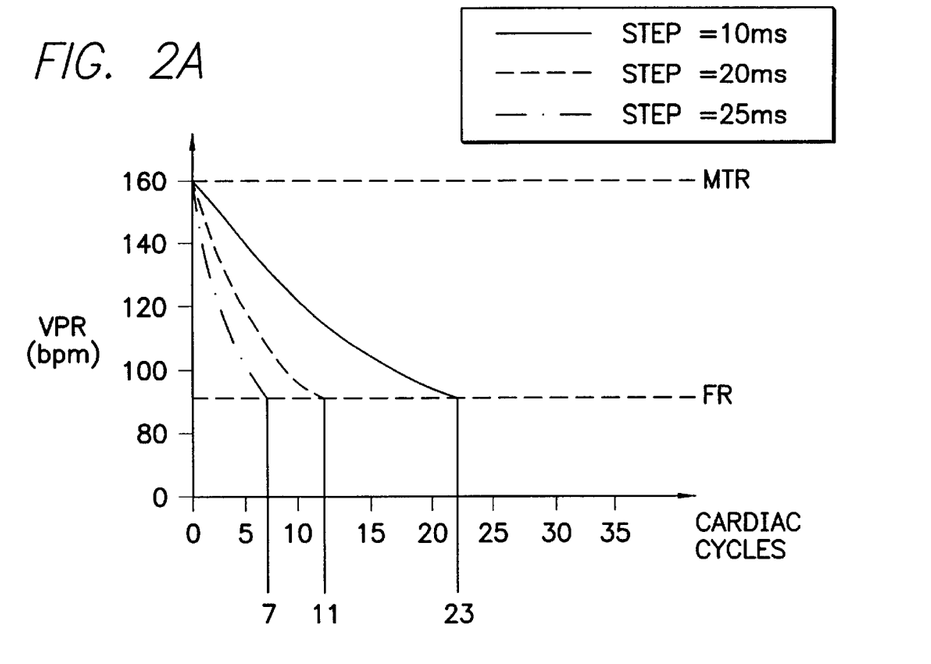
FIG. 2A depicts a graph showing a curvilinear decrease in rate when the programmable steps are based on an interval (ms) change.

Referring now to FIG. 2A, a graph showing the number of cardiac cycles necessary for the ventricular pacing rate to drop from the MTR to the fallback rate is described for three different fallback step values. The MTR is assumed to be 160 bpm, the fallback rate is assumed to be 90 bpm, and the initial ventricular pacing interval is assumed to be 375 ms (corresponding to an initial ventricular pacing rate of 160 bpm). If the fallback step is set to 10 ms, the ventricular pacing interval increases by 10 ms each cardiac cycle. Correspondingly, the ventricular pacing rate decreases by approximately 3 bpm each cardiac cycle. As a result, with a fallback step value of 10 ms, the ventricular pacing rate will drop from the MTR to the fallback rate in 23 cardiac cycles. Increasing the value of the fallback step to 20 ms results in the ventricular pacing rate reaching the fallback rate in 11 cardiac cycles, while further increasing the fallback step to 25 ms results in the ventricular pacing rate reaching the fallback rate in 7 cardiac cycles.

Figure 2B:
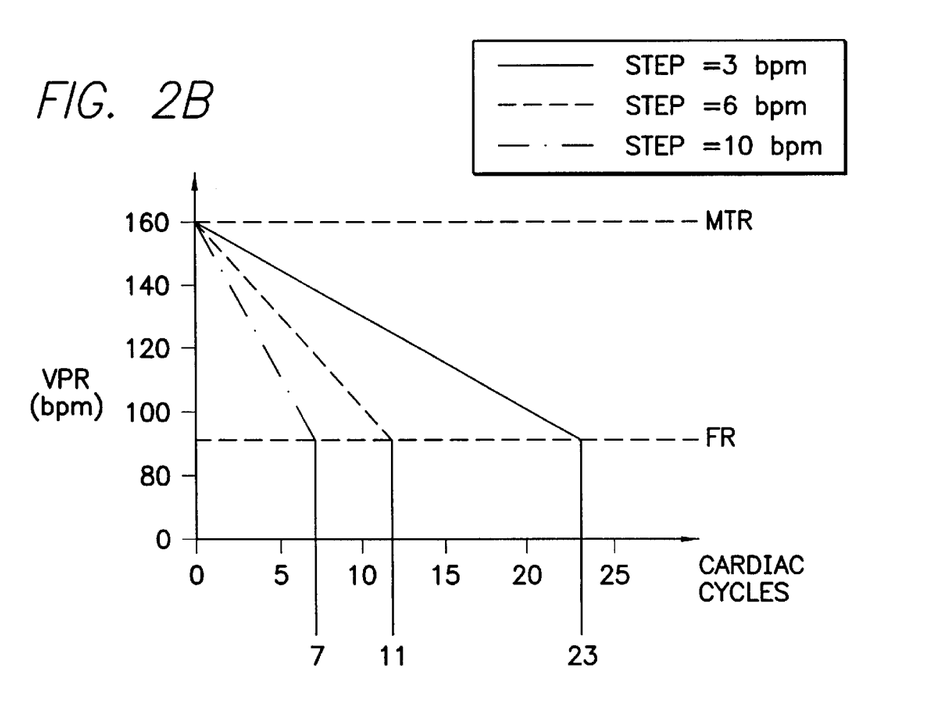
FIG. 2B depicts a graph showing a linear decrease in rate when the programmable steps are based on rate (ppm) changes.

Optionally, the progressive reduction of the ventricular pacing rate to the fallback rate may be accomplished by reducing the ventricular pacing rate directly rather than via the ventricular pacing interval. Using this approach the fallback step is expressed as a pacing rate. For example, the ventricular pacing rate may be reduced by a fallback step of 3 bpm every cardiac cycle until the fallback rate is reached. Referring to FIG. 2B, a graph showing the number of cardiac cycles necessary for the ventricular pacing rate to drop from the MTR to the fallback rate is shown for fallback step values of 3 bpm, 6 bpm, and 10 bpm, with the same parameters as assumed for FIG. 2A. Similarly to the graph of FIG. 2A, the fallback rate is reached in 7, 11, and 23 cardiac cycles for the fallback step values of 10 bpm, 6 bpm, and 3 bpm respectively. The difference between reducing the ventricular pacing rate directly or indirectly (by increasing the ventricular pacing interval), is that in case of the direct reduction, the progressive decrease in the ventricular pacing rate is linear (as shown in FIG. 2B), while in case of the indirect reduction, the progressive decrease is curvilinear (as shown in FIG. 2A).

Thus, the medical practitioner can adjust the time necessary for the ventricular pacing rate to reach the fallback rate by increasing or decreasing the value of the fallback step.

The pacemaker 10 (FIG. 1) as described thus far operates similarly to previously known pacemakers, except that previously known pacemakers differ from the pacemaker 10 (FIG. 1) in that they initiate the fallback response at the MTR. As a result, previously known pacemakers enter the fallback response even if the patient's intrinsic atrial rate slightly exceeds the MTR due to the patient's level of activity or an excited emotional state. In addition, previously known pacemakers exit the fallback response as soon as the intrinsic atrial rate drops below the MTR, even though this drop may last only several cardiac cycles. This approach may result in the pacemaker frequently entering and exiting the fallback response if the intrinsic atrial rate dips below the MTR every few cardiac cycles (e.g. as would occur if the patient was engaging in a sporadic physical activity such as climbing stairs).

Figure 3:
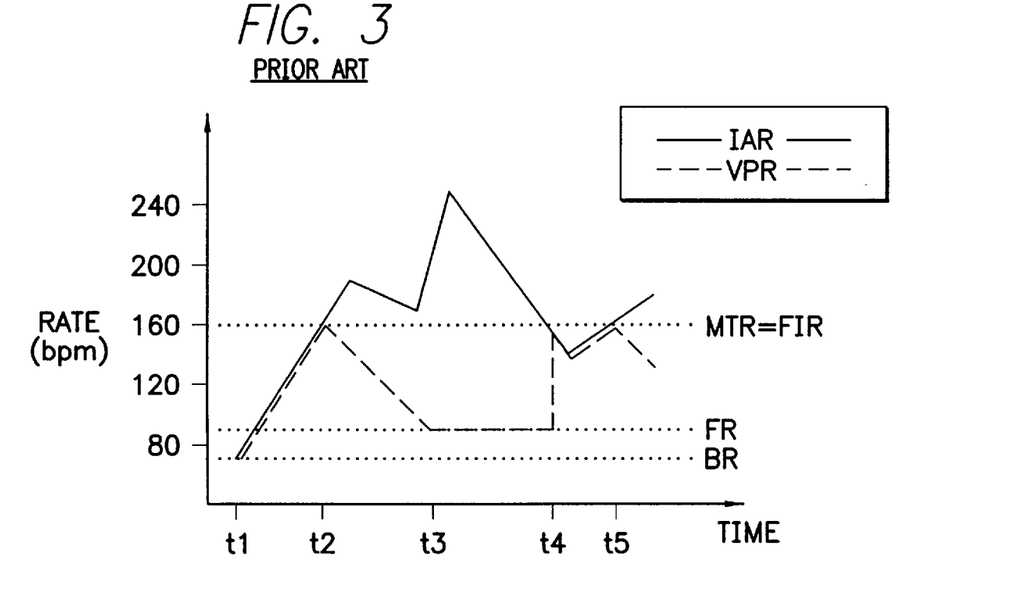
FIG. 3 depicts a graph of the intrinsic atrial rate and the ventricular pacing rate plotted over time, representing standard fallback response operation of a previously known pacemaker.
Figure 4:
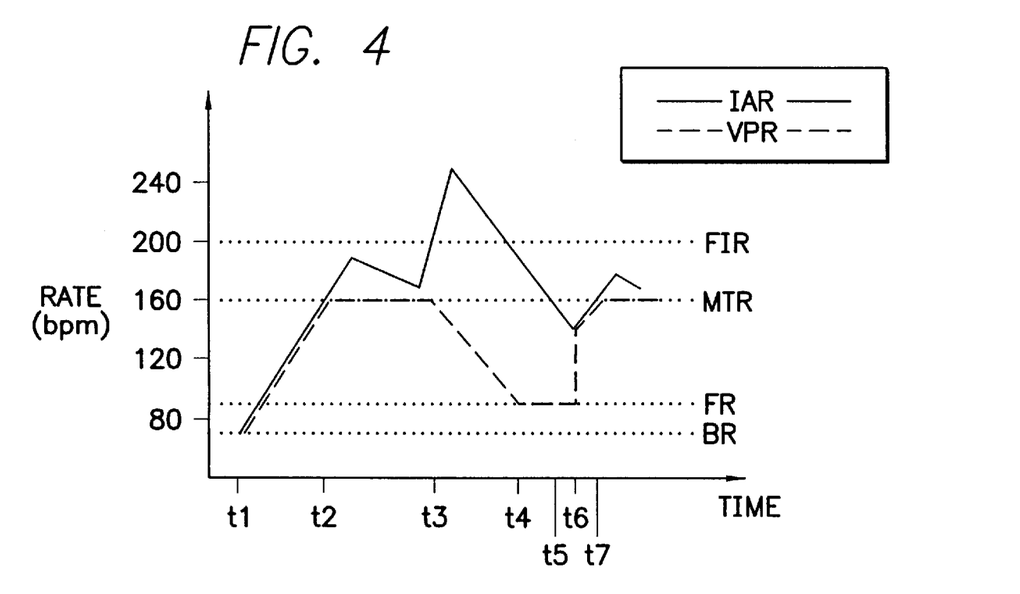
FIG. 4 depicts a graph of the intrinsic atrial rate and the ventricular pacing rate plotted over time, representing fallback response operation of the pacemaker of FIG. 1 in accordance with the principles of the present invention.

The differences in operation between previously known pacemakers and the pacemaker 10 (FIG. 1) of the present invention may be better understood by reference to FIGS. 3 and 4, and accompanying descriptions.

Referring now to FIG. 3, a graph depicting an example of the fallback response of a previously known pacemaker is described. In this example, the MTR is 160 bpm, the fallback initiating rate is equal to the MTR, or 160 bpm, the fallback rate is 90 bpm, and the base rate is 70 bpm.

Before t1, when the intrinsic atrial rate is below the base rate, the ventricular pacing rate is equal to the base rate (70 bpm). At t1, the intrinsic atrial rate begins to increase until t2 when the intrinsic atrial rate reaches the MTR of 160 bpm. From t1 to t2 the ventricular pacing rate is equal to the intrinsic atrial rate, since in order to maintain 1:1 AV synchrony it is preferable to pace the ventricles at the intrinsic atrial rate. At t2 the pacemaker initiates the fallback response since the intrinsic atrial rate exceeds the MTR (and thus the fallback initiating rate). From t2 to t3 the ventricular pacing rate decreases until the fallback rate of 90 bpm is reached at t3. From t3 to t4 the ventricular pacing rate is equal to the fallback rate since the intrinsic atrial rate stays above the MTR. At t4 the intrinsic atrial rate drops below the MTR and the pacemaker instantly switches the ventricular pacing rate from the fallback rate to the intrinsic atrial rate. From t4 to t5 the intrinsic atrial rate is below the MTR and thus the ventricular pacing rate is equal to the intrinsic atrial rate. However, at t5 the intrinsic atrial rate exceeds the MTR again and the fallback response is initiated.

The approach of previously known pacemakers may be problematic, as discussed above, because the fallback response is initiated as soon as the intrinsic atrial rate exceeds the MTR. As a result, when the intrinsic atrial rate slightly exceeds the MTR (from t2 to t3) the patient was unnecessarily subjected to progressively slower ventricular pacing (resulting in lower cardiac output), possibly at a time when the patient needed a higher cardiac output (such as during physical activity or an excited emotional state causing the elevated intrinsic atrial rate). In addition, the ventricular pacing rate switches back to the intrinsic atrial rate from the fallback rate as soon as the intrinsic atrial rate drops below the MTR. As a result, the ventricular pacing rate was switched from 90 bpm to 160 bpm before the pacemaker verified that the drop in the intrinsic atrial rate lasted for more than a few cycles. Furthermore, at t5 the fallback response was initiated again as soon as the intrinsic atrial rate exceeded the MTR with possible discomfort to the patient if the high intrinsic atrial rate was due to physical activity or an excited emotional state.

Another prior art approach to fallback response, initiates the fallback response, subsequent to the intrinsic atrial rate exceeding the MTR, after waiting a predetermined amount of time. This approach is problematic because if the patient experiences a high intrinsic atrial rate due to physical activity or an excited emotional state for a longer time than the predetermined amount, the fallback response would be initiated even though the high intrinsic atrial rate is not pathologic.

The pacemaker 10 (FIG. 1) of the present invention solves the above problems, first by initiating the fallback response at fallback initiating rate higher than the MTR, and second by exiting the fallback response only when fallback exit criteria are met by the intrinsic atrial rate. A fallback initiating rate higher than the MTR ensures that a high non-pathological intrinsic atrial rate, which exceeds the MTR, but is below the fallback initiating rate, will not cause the pacemaker 10 (FIG. 1) to initiate the fallback response. Selection of fallback initiating rate higher than the MTR is made possible by the pacemaker 10 (FIG. 1) continually monitoring the intrinsic atrial rate as it exceeds the MTR by sensing all P-waves, even the P-waves occurring during the TARP. A system for sensing P-waves occurring during the TARP is disclosed in above-incorporated U.S. Pat. No. 4,944,928 of Sholder. The fallback exit criteria function causes the pacemaker 10 (FIG. 1) to remain in the fallback response until the lower intrinsic atrial rate satisfies the criteria. This function avoids unnecessary switching in and out of the fallback response which may occur in previously known pacemakers as described above.

Referring now to FIG. 4, a graph depicting an example of the fallback response of the pacemaker 10 (FIG. 1) of the present invention is described. In this example, the MTR is 160 bpm, the fallback initiating rate is 200 bpm, the fallback rate is 90 bpm, and the base rate is 70 bpm.

Before t1, when the intrinsic atrial rate is below the base rate, the atrial ventricular pacing rate is equal to the base rate (70 bpm). At t1, the intrinsic atrial rate begins to increase and is tracked results in an identical ventricular posed rate until t2 when the intrinsic atrial rate reaches the MTR of 160 bpm. From t1 to t2 the ventricular pacing rate is equal to the intrinsic atrial rate, since in order to maintain AV synchrony it is preferable to pace the ventricles at the intrinsic atrial rate. At t2, when the intrinsic atrial rate exceeds the MTR, the ventricular pacing rate is set equal to the MTR (and the unit functions in either the 2:1 block or Wenckebach response). From t2 to t3, when the intrinsic atrial rate is above the MTR but below the fallback initiating rate, the ventricular pacing rate is equal to the MTR (and the unit functions in either the 2:1 block or Wenckebach response). The ventricular pacing rate is set to such a high value because the intrinsic atrial rate between t2 and t3 is most likely due to physical activity or an excited emotional state (normal physiologic response). A high ventricular pacing rate will provide an appropriately high level of cardiac output needed by the patient.

At t3 the intrinsic atrial rate exceeds the fallback initiating rate and the fallback response is initiated. From t3 to t4 the ventricular pacing rate progressively decreases in programmable fallback steps, as discussed above in connection with FIGS. 2A and 2B, until it reaches the fallback rate at t4. From t4 to t5 the ventricular pacing rate is equal to the fallback rate. At t5 the intrinsic atrial rate drops below the MTR and the pacemaker 10 (FIG. 1) begins monitoring the intrinsic atrial rate in accordance with fallback exit criteria programmed by the medical practitioner. The fallback exit criteria are described in greater detail below in connection with FIG. 5. From t5 to t6 the ventricular pacing rate remains at the fallback rate as the intrinsic atrial rate is monitored to ensure that the fallback exit criteria are met before the ventricular pacing rate is set to the intrinsic atrial rate. At t6 the criteria are met and the pacemaker 10 (FIG. 1) exits the fallback response and sets the ventricular pacing rate equal to the intrinsic atrial rate, thus regaining AV synchrony. From t6 to t7 the ventricular pacing rate is equal to the intrinsic atrial rate. At t7 the intrinsic atrial rate increases above the MTR, and the ventricular pacing rate is set to the MTR.

Thus, the pacemaker 10 (FIG. 1) of the present invention avoids entering the fallback response based on a non-pathologic high intrinsic atrial rate, as may occur in the previously known pacemakers. In addition, the pacemaker 10 (FIG. 1) prevents switching in and out of the fallback response when the intrinsic atrial rate oscillates slightly above and below the MTR, by only exiting the fallback response when programmable fallback exit criteria are met.

Figure 5:
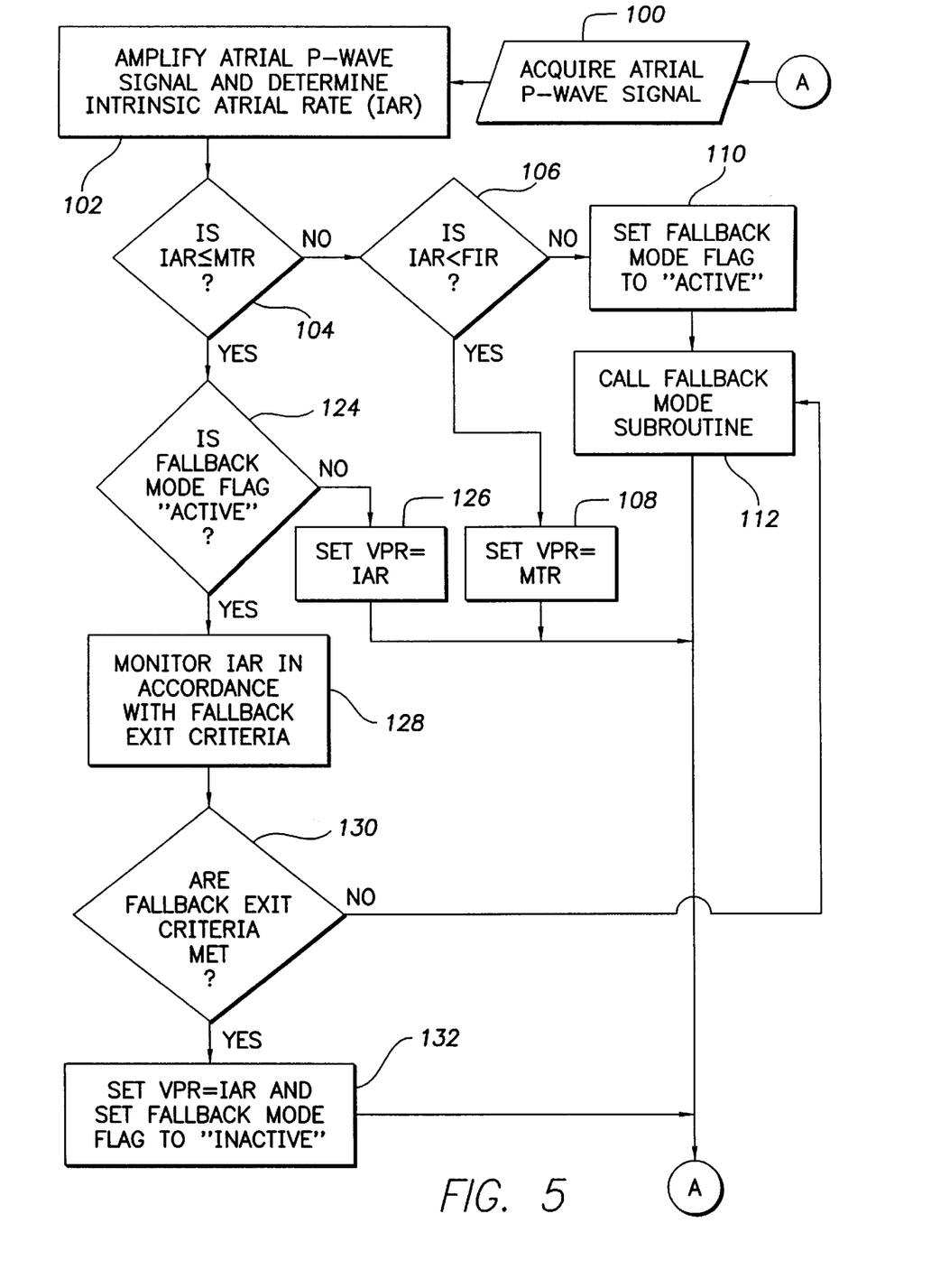
FIG. 5 is a logic flow diagram representing a fallback response control program executed by the control system of the pacemaker of FIG. 1 in accordance with the principles of the present invention.

Referring now to FIG. 5, a logic flow diagram representing the control program for the control system 30 of FIG. 1 in accordance with the present invention is described. This control program is executed in a loop, continually providing the pacemaker 10 (FIG. 1) with the capability of controlling the fallback response. Preferably, one complete loop of the control program follows a single cardiac cycle.

After the control program begins at a step 100, the control system 30 (FIG. 1) causes the pacemaker 10 (FIG. 1) to acquire a P-wave signal from the atria (not shown) of the heart 12 (FIG. 1) through the electrode 18 (FIG. 1). At a step 102, the control system 30 (FIG. 1) causes the atrial amplifier 26 (FIG. 1) to amplify the P-wave signal, and then receives the amplified P-wave signal through the signal line 32 (FIG. 1). At the step 102, the control system 30 (FIG. 1) also determines the intrinsic atrial rate as described above.

At a test 104 the control system 30 (FIG. 1) determines if the intrinsic atrial rate is less than or equal to the MTR. If the intrinsic atrial rate is greater than the MTR, at a test 106 the control system 30 (FIG. 1) determines if the intrinsic atrial rate is less than the fallback initiating rate. If the intrinsic atrial rate is less than the fallback initiating rate, at a step 108 the ventricular pacing rate is set equal to the MTR. The step 108 keeps the ventricular pacing rate at the MTR when the intrinsic atrial rate is between the MTR and the fallback initiating rate, to ensure proper cardiac output at a non-pathologic high intrinsic atrial rate when the patient is engaging in physical activity or is in an excited emotional state. The control system 30 (FIG. 1) then completes the loop by returning to the step 100 for the next cardiac cycle.

If, at the test 106, the control system 30 (FIG. 1) determines that the intrinsic atrial rate is greater than or equal to the fallback initiating rate, the intrinsic atrial rate is indicative of a pathologic atrial arrhythmia. Thus, at a step 110, the fallback response is initiated by setting a fallback response flag to "active". The fallback response flag indicates whether the pacemaker 10 (FIG. 1) is in the fallback response during the current program cycle depending on whether the flag is set to "active" (i.e., the pacemaker 10 (FIG. 1) is in the fallback response, or "inactive" (i.e., the pacemaker 10 (FIG. 1) is not in the fallback response). The initial, default state for the fallback response flag is "inactive."

At a step 112 a fallback response subroutine is called. Subroutines are known in the computer programming art as functions designed to perform specific tasks requested by the main program. One of the advantages of using subroutines is that two or more programs can use the same subroutine to perform a particular function. Modern programming techniques also encompass programmable "objects" which function similarly to subroutines. The main advantage of programmable "objects" is that once an "object" is developed to perform a particular function, it may be used in any program in which it is desired to use that function.

Figure 6:
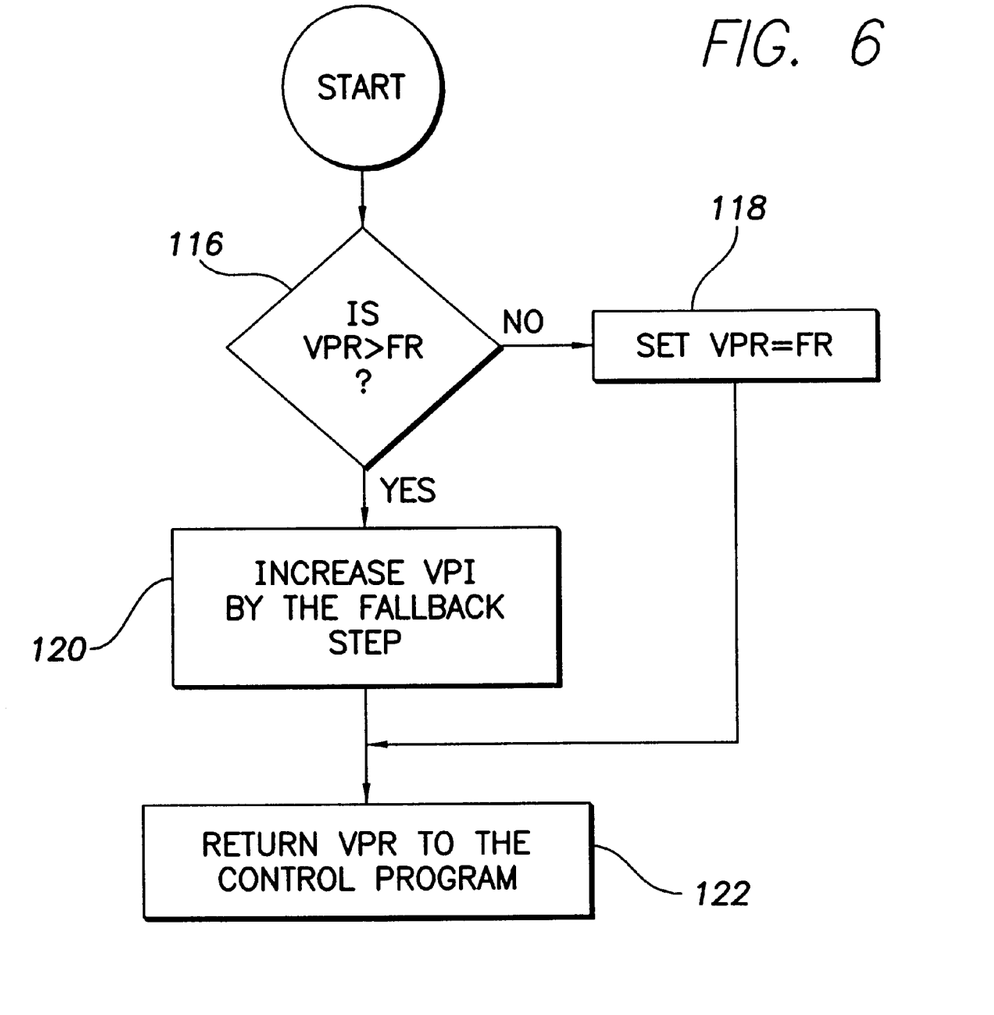
FIG. 6 is a logic flow diagram representing a fallback response subroutine executed by the control system of the pacemaker of FIG. 1 for incrementally reducing the ventricular pacing rate to the fallback rate in accordance with the principles of the present invention.

The fallback response subroutine, shown in FIG. 6, enables the control system 30 (FIG. 1) to progressively decrease the ventricular pacing rate in incremental fallback steps preferably at one fallback step per program cycle until the ventricular pacing rate reaches the fallback rate. The number of program cycles necessary for the ventricular pacing rate to decrease from its maximum value (i.e. equal to the MTR) to the fallback rate is a function of the size of the fallback step as discussed above in connection with FIGS. 2A and 2B.

The fallback response subroutine begins at a test 116, where the control system 30 (FIG. 1) determines whether the ventricular pacing rate is greater than the fallback rate. If the ventricular pacing rate is less than or equal to the fallback rate, the ventricular pacing rate is set equal to the fallback rate at a step 118. Because a decrease in the ventricular pacing rate during the previous program cycle could bring the ventricular pacing rate below the fallback rate, the step 118 ensures that the ventricular pacing rate is set to the fallback rate if such an "overshoot" occurs. An overshoot is especially likely to occur if the fallback step is set to a high value causing the ventricular pacing rate to drop several bpm per program cycle. In addition, if the fallback rate is actually a variable base rate which may have increased or decreased since the last program cycle, the step 118 synchronizes the ventricular pacing rate with the fallback rate if the ventricular pacing rate of the current program cycle is lower than the fallback rate.

If, at the test 116, the control system 30 (FIG. 1) determines that the ventricular pacing rate (VPR) is greater than the fallback rate, the control system 30 (FIG. 1) proceeds to a step 120. At the step 120, the control system 30 (FIG. 1) increases the ventricular pacing interval (VPI) by the fallback step. The increase of the ventricular pacing interval results in a reduction of the ventricular pacing rate by a number of bpm proportional to the size of the fallback step. Referring again to FIG. 2A, if the fallback step is set to 10 ms, the ventricular pacing rate decreases by approximately 3 bpm per cardiac or program cycle, taking 23 cycles to decrease from the MTR (160 bpm) to the fallback rate (90 bpm). However, if the fallback step is set to 20 ms, the ventricular pacing rate decreases by approximately 6 bpm per cardiac or program cycle, taking 11 cycles to decrease from the MTR to the fallback rate. If the optional approach of reducing the ventricular pacing rate directly (as described above in connection with FIG. 2B) is used and the fallback step is defined in terms of a pacing rate, at the step 120, the control system 30 (FIG. 1) decreases the VPR by the fallback step directly. Returning now to FIG. 6, at a step 122 the fallback response subroutine returns the ventricular pacing rate to the control program.

Returning now to FIG. 5, if at the test 104 the control system 30 (FIG. 1) determines that the intrinsic atrial rate is less than or equal to the MTR, the control system 30 (FIG. 1) proceeds to a test 124. At the test 124, the control system 30 (FIG. 1) determines whether the fallback response flag is set to "active." Thus the test 124 determines whether the pacemaker 10 (FIG. 1) is currently in the fallback response.

If the fallback response flag is "inactive," at a step 126 the ventricular pacing rate is set to the intrinsic atrial rate restoring 1:1 AV synchrony. The step 126 ensures that 1:1 AV synchrony is maintained by pacing the ventricles at the intrinsic atrial rate when the pacemaker 10 (FIG. 1) is not in the fallback response and when the intrinsic atrial rate is less than or equal to the MTR. The control system 30 (FIG. 1) then completes the loop by returning to the step 100 for the next cardiac cycle.

If the fallback response flag is "active," at a step 128 the intrinsic atrial rate is monitored in accordance with the fallback exit criteria programmed by the medical practitioner. As discussed above, the primary purpose of the fallback exit criteria is to prevent the exit from the fallback response based on an intrinsic atrial rate which drops below the MTR for only a few cardiac cycles. Consequently, the preferred form of implementation of the fallback exit criteria is an incremental counter which counts the number of cardiac cycles the intrinsic atrial rate has been below the MTR. If the intrinsic atrial rate has remained below the MTR for a certain number of cardiac cycles (programmed by the medical practitioner as the fallback exit criteria—20–30 cardiac cycles, for example) the criteria have been satisfied. However, if the intrinsic atrial rate increases above the MTR before the criteria is met, the counter is reset to zero.

The fallback exit criteria may be implemented in other ways without departing from the spirit of the present invention. For example, the intrinsic atrial rate may be monitored against a real-time clock, with the fallback exit criteria being a certain amount of time (20 seconds for example) for which the intrinsic atrial rate must remain below the MTR in order for the criteria to be met. Another example of fallback exit criteria is a fallback exit rate, where if the intrinsic atrial rate reaches the fallback exit rate while the fallback response flag is "active", the fallback exit criteria are met. Optionally, the medical practitioner may define several fallback criteria in combination so that more than one criterion must be met in order for the criteria to be satisfied.

At a test 130 the control system 30 (FIG. 1) determines if the fallback exit criteria have been met at the step 128. If the fallback exit criteria is not met, the control system 30 (FIG. 1) proceeds to the step 112 and calls the fallback response subroutine, described above in connection with FIG. 6, to continue the fallback response operation by either decreasing the ventricular pacing rate if the ventricular pacing rate is above the fallback rate, or by setting the ventricular pacing rate equal to the fallback rate if the ventricular pacing rate is below the fallback rate. The control system 30 (FIG. 1) then completes the loop by returning to the step 100 for the next cardiac cycle. If at the test 130 the fallback exit criteria is met, at a step 132, the control system 30 (FIG. 1) sets the ventricular pacing rate to the intrinsic atrial rate restoring 1:1 AV synchrony, and also causes the pacemaker 10 (FIG. 1) to exit the fallback response by setting the fallback flag to "inactive." The step 132 ensures that the fallback response is exited and normal operation is restored only when the intrinsic atrial rate meets the fallback exit criteria. The control system 30 (FIG. 1) then completes the loop by returning to the step 100 for the next cardiac cycle.

Thus, an implantable dual-chamber pacemaker programmed to operate primarily in a P-wave tracking mode is provided, where the pacemaker switches to a fallback response at a threshold rate higher than a maximum tracking rate of the pacemaker. The pacemaker of the present invention exits the fallback response when programmable fallback exit criteria are met.

One skilled in the art will appreciate that the present invention can be practiced by other than the described embodiments, which are presented for purposes of illustration and not of limitation, and the present invention is limited only by the claims that follow.

What is claimed is:

1. An implantable pacemaker comprising:

first and second leads coupling the pacemaker to, respectively, an atrial chamber and a ventricular chamber of a heart;

atrial sense circuitry for sensing an intrinsic atrial rate through the first lead;

pulse generating circuitry for generating pacing pulses for delivery to the atrial and ventricular chambers through, respectively, the first and second leads, wherein the pulse generating circuitry generates pacing pulses for delivery to the ventricular chambers at a ventricular pacing rate not less than a first threshold rate and not greater than a second threshold rate; and a control system, coupled to the atrial sense circuitry and to the pulse generating circuitry, for initiating a fallback response when the intrinsic atrial rate exceeds a third programmable threshold rate higher than the second threshold rate, wherein the control system is operable to monitor the intrinsic atrial rate in accordance with at least one programmable fallback exit criterion when the pacemaker is in the fallback response and the intrinsic atrial rate drops below the second threshold rate; and wherein the control system is operable to exit the fallback response and set the ventricular pacing rate equal to the intrinsic atrial rate when the at least one fallback exit criterion is met.

2. The pacemaker of claim 1, wherein the at least one programmable exit criterion comprises a delay comprising a plurality of cardiac cycles.

3. The pacemaker of claim 1, wherein the at least one programmable exit criterion comprises a time delay of a programmable duration.

4. The pacemaker of claim 1, wherein the at least one programmable exit criterion comprises a fourth threshold rate higher than the first threshold rate but lower than the second threshold rate, and wherein the at least one programmable exit criterion is satisfied if the intrinsic atrial rate is lower than or equal to the fourth threshold rate while the pacemaker is in the fallback response.

5. The pacemaker of claim 4, wherein the control system, when the fallback response is initiated, is operable to:

incrementally decrease the ventricular pacing rate by a programmable second fallback step during each cardiac cycle, beginning with the cardiac cycle during which the fallback response was initiated;

end the incremental decrease of the ventricular pacing rate when the ventricular pacing rate is less than or equal to a fifth threshold rate which is lower than the second threshold rate and greater than or equal to the first threshold rate; and set the ventricular pacing rate equal to the fifth threshold rate when the ventricular pacing rate decreases below the fifth threshold rate.

6. The pacemaker of claim 1, wherein the at least one programmable exit criterion comprises a plurality of programmable exit criteria, and wherein the at least one programmable exit criterion is satisfied when each criterion of the plurality of programmable exit criteria is satisfied.

7. The pacemaker of claim 4, wherein the control system operatively defines a ventricular pacing interval inversely proportional to the ventricular pacing rate, and wherein the control system, when the fallback response is initiated, is operable to:

incrementally increase the ventricular pacing interval by a programmable first fallback step during each cardiac cycle, beginning with the cardiac cycle during which the fallback response was initiated, to cause the ventricular pacing rate to decrease by an amount proportional to the value of the first fallback step;

end the incremental increase of the ventricular pacing interval when the ventricular pacing rate is less than or equal to a fifth threshold rate which is lower than the second threshold rate and greater than or equal to the first threshold rate;

set the ventricular pacing rate equal to the fifth threshold rate when the ventricular pacing rate decreases below the fifth threshold rate; and determine the intrinsic atrial rate by causing the atrial sense circuitry to sense all atrial events of each cardiac cycle, including atrial events occurring during a total refractory period of each cardiac cycle.

8. The pacemaker of claim 1, wherein the control system is operable to set the ventricular pacing rate equal to the second threshold rate when the intrinsic atrial rate is greater than or equal to the second threshold rate but is less than the third threshold rate and the pacemaker is not in the fallback response.

9. An implantable pacemaker comprising:

first and second leads coupling the pacemaker to, respectively, an atrial chamber and a ventricular chamber of a heart;

atrial sense circuitry for sensing an intrinsic atrial rate through the first lead;

pulse generating circuitry for generating pacing pulses for delivery to the atrial and ventricular chambers through, respectively, the first and second leads, wherein the pulse generating circuitry generates pacing pulses for delivery to the ventricles at a ventricular pacing rate not less than a first threshold rate and not greater than a second threshold rate; and a control system, coupled to the atrial sense circuitry and to the pulse generating circuitry, for exiting a fallback response, wherein when the pacemaker is in the fallback response and the intrinsic atrial rate is less than or equal to the second threshold rate the control system is operable to:

monitor the intrinsic atrial rate in accordance with at least one programmable fallback exit criterion; and when the at least one fallback exit criterion is met, the control system is operable to exit the fallback response and set the ventricular pacing rate equal to the intrinsic atrial rate.

10. The pacemaker of claim 9, wherein the at least one programmable exit criterion comprises a delay comprising a plurality of cardiac cycles.

11. The pacemaker of claim 9, wherein the at least one programmable exit criterion comprises a time delay of a programmable duration.

12. The pacemaker of claim 9, wherein the at least one programmable exit criterion comprises a fourth threshold rate higher than the first threshold rate but lower than the second threshold rate, and wherein the at least one programmable exit criterion is satisfied if the intrinsic atrial rate is lower than or equal to the fourth threshold rate while the pacemaker is in the fallback response.

13. The pacemaker of claim 9, wherein the at least one programmable exit criterion comprises a plurality of programmable exit criteria, and wherein the at least one programmable exit criterion is satisfied when each criterion of the plurality of programmable exit criteria is satisfied.

14. The pacemaker of claim 9, wherein the control system is coupled to the atrial sense circuitry and to the pulse generating circuitry, and wherein the control system initiates the fallback response when the intrinsic atrial rate exceeds a third programmable threshold rate higher than the second threshold rate.

15. An implantable pacemaker comprising:

first and second leads coupling the pacemaker to, respectively, an atrial chamber and a ventricular chamber of a heart;

atrial sense circuitry for sensing an intrinsic atrial rate through the first lead;

pulse generating circuitry for generating pacing pulses for delivery to the atrial and ventricular chambers through, respectively, the first and second leads; and a control system, coupled to the atrial sense circuitry and also coupled to the pulse generating circuitry, for pacing the ventricular chambers;

the control system is operable to monitor the intrinsic atrial rate in accordance with at least one programmable fallback exit criterion when the pacemaker is in the fallback response and the intrinsic atrial rate is less than or equal to the MTR;

wherein the control system is operable to exit the fallback response and set the ventricular pacing rate equal to the intrinsic atrial rate when the at least one fallback exit criterion is met; and wherein the ventricular chambers are paced at a ventricular pacing rate at least equal to a base rate, and at most equal to a maximum tracking rate (MTR); and wherein the control system is operable to:

define a ventricular pacing interval inversely proportional to the ventricular pacing rate, determine the intrinsic atrial rate by causing the atrial sense circuitry to sense all atrial events of each cardiac cycle, including atrial events occurring during a total atrial refractory period of each cardiac cycle, and initiate a fallback response when the intrinsic atrial rate exceeds a fallback initiating rate higher than the MTR.

16. The pacemaker of claim 15, wherein when the fallback response is initiated the control system is operable to:

incrementally increase the ventricular pacing interval by a programmable first fallback step during each cardiac cycle, beginning with the cardiac cycle during which the fallback response was initiated, to cause the ventricular pacing rate to decrease by an amount proportional to the value of the first fallback step;

end the incremental increase of the ventricular pacing interval when the ventricular pacing rate is less than or equal to a fallback rate which is lower than the MTR but is greater than or equal to the base rate; and set the ventricular pacing rate equal to the fallback rate when the ventricular pacing rate decreases below the fallback rate.

17. The pacemaker of claim 15, wherein when the intrinsic atrial rate is greater than or equal to the MTR but is less than the fallback initiating rate and the pacemaker is not in the fallback response, the control system is operable to set the ventricular pacing rate equal to the MTR.

18. The pacemaker of claim 15, wherein the at least one programmable exit criterion comprises a delay comprising a plurality of cardiac cycles.

19. The pacemaker of claim 15, wherein the at least one programmable exit criterion comprises a time delay of a programmable duration.

20. The pacemaker of claim 15, wherein the at least one programmable exit criterion comprises a fourth threshold rate higher than the first threshold rate but lower than the second threshold rate, and wherein the at least one programmable exit criterion is satisfied if the intrinsic atrial rate is lower than or equal to the fourth threshold rate while the pacemaker is in the fallback response.

21. The pacemaker of claim 15, wherein the at least one programmable exit criterion comprises a plurality of programmable exit criteria, and wherein the at least one programmable exit criterion is satisfied when each criterion of the plurality of programmable exit criteria is satisfied.

22. An implantable pacemaker comprising:

lead means for coupling the pacemaker to, respectively, an atrial chamber and a ventricular chamber of a heart;

atrial sensing means for sensing an intrinsic atrial rate in the atrial chamber of a heart, the atrial sensing means comprising means for sensing atrial events during a total refractory period;

pulse generating means for generating pacing pulses for delivery to the atrial and ventricular chambers at a ventricular pacing rate not less than a first threshold rate and not greater than a second threshold rate;

means for defining a ventricular pacing interval inversely proportional to the ventricular pacing rate;

first trigger means for initiating a fallback response when the intrinsic atrial rate exceeds a third threshold rate higher than the second threshold rate;

first testing means for determining when the intrinsic atrial rate is less than or equal to the second threshold rate;

first monitoring means responsive to the first testing means for monitoring the intrinsic atrial rate in accordance with at least one programmable fallback exit criterion when the pacemaker is in the fallback response and the intrinsic atrial rate is less than or equal to the second threshold rate;

second testing means for determining when the at least one fallback exit criterion is met;

second trigger means responsive to the second testing means for exiting the fallback response when the at least one fallback exit criterion is met; and first selection means responsive to the second trigger means for setting the ventricular pacing rate equal to the intrinsic atrial rate when the fallback response is exited.

23. The pacemaker of claim 22, wherein the at least one programmable exit criterion comprises a delay comprising a plurality of cardiac cycles.

24. The pacemaker of claim 22, wherein the at least one programmable exit criterion comprises a time delay of a programmable duration.

25. The pacemaker of claim 22, wherein the at least one programmable exit criterion comprises a fourth threshold rate higher than the first threshold rate but lower than the second threshold rate, and wherein the at least one programmable exit criterion is satisfied if the intrinsic atrial rate is lower than or equal to the fourth threshold rate while the pacemaker is in the fallback response.

26. The pacemaker of claim 25, further comprising:

incrementing means for incrementally increasing the ventricular pacing interval by a programmable first fallback step during each cardiac cycle, beginning with the cardiac cycle during which the fallback response is initiated, to cause the ventricular pacing rate to decrease by an amount proportional to the value of the first fallback step;

second monitoring means for determining when the ventricular pacing rate is less than or equal to a fifth threshold rate which is lower than the second threshold rate and greater than or equal to the first threshold rate;

second selection means responsive to the second monitoring means for ending the incremental increase of the ventricular pacing interval when the ventricular pacing rate is less than or equal to the fifth threshold rate; and third selection means responsive to the second monitoring means for setting the ventricular pacing rate equal to the fifth threshold rate when the ventricular pacing rate is less than the fifth threshold rate.

27. The pacemaker of claim 22, wherein the at least one programmable exit criterion comprises a plurality of programmable exit criteria, and wherein the at least one programmable exit criterion is satisfied when each criterion of the plurality of programmable exit criteria is satisfied.

28. The pacemaker of claim 22, further comprising:
third monitoring means for determining when the intrinsic atrial rate is greater than the second threshold rate, but is less than the third threshold rate; and
fourth selection means responsive to the third monitoring means for setting the ventricular pacing rate equal to the second threshold rate when the intrinsic atrial rate is greater than or equal to the second threshold rate but is less than the third threshold rate and the pacemaker is not in the fallback response.

29. An implantable pacemaker comprising:
lead means for coupling the pacemaker to, respectively, an atrial chamber and a ventricular chamber of a heart;
atrial sensing means for sensing an intrinsic atrial rate in the atrial chamber of a heart, the atrial sensing means comprising means for sensing atrial events during a total refractory period;
pulse generating means for generating pacing pulses for delivery to the atrial and ventricular chambers at a ventricular pacing rate not less than a first threshold rate and not greater than a second threshold rate;
means for defining a ventricular pacing interval wherein the ventricular pacing interval is inversely proportional to the ventricular pacing rate;
first testing means for determining when the intrinsic atrial rate is less than or equal to the second threshold rate;
first monitoring means responsive to the first testing means for monitoring the intrinsic atrial rate in accordance with at least one programmable fallback exit criterion when the pacemaker is in the fallback response and the intrinsic atrial rate is less than or equal to the second threshold rate;
second testing means for determining when the at least one fallback exit criterion is met;
second trigger means responsive to the second testing means for exiting the fallback response when the at least one fallback exit criterion is met; and
first selection means responsive to the second trigger means for setting the ventricular pacing rate equal to the intrinsic atrial rate when the fallback response is exited.

30. The pacemaker of claim 29, wherein the at least one programmable exit criterion comprises a delay comprising a plurality of cardiac cycles.

31. The pacemaker of claim 29, wherein the at least one programmable exit criterion comprises a time delay of a programmable duration.

32. The pacemaker of claim 29, wherein the at least one programmable exit criterion comprises a fourth threshold rate higher than the first threshold rate but lower than the second threshold rate, and wherein the at least one programmable exit criterion is satisfied if the intrinsic atrial rate is lower than or equal to the fourth threshold rate while the pacemaker is in the fallback response.

33. The method of claim 32, further comprising the steps of:
incrementally decreasing the ventricular pacing rate by a programmable second fallback step of a predetermined value during each cardiac cycle, beginning with the cardiac cycle during which the fallback response was initiated;
ending the incremental increase of the ventricular pacing interval when the ventricular pacing rate is less than or equal to a fifth threshold rate which is lower than the second threshold rate and greater than or equal to the first threshold rate; and
setting the ventricular pacing rate equal to the fifth threshold rate when the ventricular pacing rate decreases below the fifth threshold rate.

34. The pacemaker of claim 29, wherein the at least one programmable exit criterion comprises a plurality of programmable exit criteria, and wherein the at least one programmable exit criterion is satisfied when each criterion of the plurality of programmable exit criteria is satisfied.

35. The pacemaker of claim 29, further comprising first trigger means for initiating the fallback response when the intrinsic atrial rate exceeds a third threshold rate higher than the second threshold rate.

36. A method of pacing a heart using an implantable pacemaker comprising the steps of:
coupling the pacemaker to, respectively, an atrial chamber and a ventricular chamber of a heart;
sensing an intrinsic atrial rate in the atrial chamber of the heart;
generating pacing pulses for delivery to the atrial and ventricular chambers at a ventricular pacing rate not less than a first threshold rate and not greater than a second threshold rate;
determining when the intrinsic atrial rate is greater than or equal to a programmable third threshold rate greater than the second threshold rate;
initiating a fallback response when the intrinsic atrial rate is greater than or equal to the third threshold rate;
monitoring the intrinsic atrial rate in accordance with at least one programmable fallback exit criterion when the pacemaker is in the fallback response and the intrinsic atrial rate is less than or equal to the second threshold rate;
determining when the at least one fallback exit criterion is satisfied;
exiting the fallback response when the at least one fallback exit criterion is satisfied; and
setting the ventricular pacing rate equal to the intrinsic atrial rate when the fallback response is exited.

37. The method of claim 36, wherein the at least one programmable exit criterion comprises a delay comprising a plurality of cardiac cycles.

38. The method of claim 36, wherein the at least one programmable exit criterion comprises a time delay of a programmable duration.

39. The method of claim 36, wherein the at least one programmable exit criterion comprises a fourth threshold rate higher than the first threshold rate but lower than the second threshold rate, and wherein the at least one programmable exit criterion is satisfied if the intrinsic atrial rate is lower than or equal to the fourth threshold rate while the pacemaker is in the fallback response.

40. The method of claim 39, further comprising the steps of:
defining a ventricular pacing interval inversely proportional to the ventricular pacing rate;
incrementally increasing the ventricular pacing interval by a programmable first fallback step of a predetermined value during each cardiac cycle, beginning with the cardiac cycle during which the fallback response was initiated, to cause the ventricular pacing rate to decrease by an amount proportional to the value of the first fallback step;

ending the incremental increase of the ventricular pacing interval when the ventricular pacing rate is less than or equal to a fifth threshold rate which is lower than the second threshold rate and greater than or equal to the first threshold rate;

setting the ventricular pacing rate equal to the fifth threshold rate when the ventricular pacing rate decreases below the fifth threshold rate; and determining the intrinsic atrial rate by causing the atrial sense circuitry to sense all atrial events of each cardiac cycle, including atrial events occurring during a total refractory period of each cardiac cycle.

41. The method of claim 36, wherein the at least one programmable exit criterion comprises a plurality of programmable exit criteria, and wherein the at least one programmable exit criterion is satisfied when each criterion of the plurality of programmable exit criteria is satisfied.

42. The method of claim 36, further comprising the steps of:

determining when the intrinsic atrial rate is greater than or equal to the second threshold rate but is less than the third threshold rate;

determining when the pacemaker is not in the fallback response; and setting the ventricular pacing rate equal to the second threshold rate when the pacemaker is not in the fallback response.

43. A method of operating an implantable pacemaker comprising the steps of:

coupling the pacemaker to, respectively, an atrial chamber and a ventricular chamber of a heart;

sensing an intrinsic atrial rate in the atrial chamber of the heart;

generating pacing pulses for delivery to the atrial and ventricular chambers at a ventricular pacing rate not less than a first threshold rate and not greater than a second threshold rate;

monitoring the intrinsic atrial rate in accordance with at least one programmable fallback exit criterion when the pacemaker is in a fallback response and the intrinsic atrial rate is less than or equal to the second threshold rate;

determining when the at least one fallback exit criterion is satisfied;

exiting the fallback response when the at least one fallback exit criterion is satisfied; and setting the ventricular pacing rate equal to the intrinsic atrial rate when the fallback response is exited.

44. The method of claim 43, wherein the at least one programmable exit criterion comprises a delay comprising a plurality of cardiac cycles.

45. The method of claim 43, wherein the at least one programmable exit criterion comprises a time delay of a programmable duration.

46. The method of claim 43, wherein the at least one programmable exit criterion comprises a fourth threshold rate higher than the first threshold rate but lower than the second threshold rate, and wherein the at least one programmable exit criterion is satisfied if the intrinsic atrial rate is lower than or equal to the fourth threshold rate while the pacemaker is in the fallback response.

47. The method of claim 43, wherein the at least one programmable exit criterion comprises a plurality of programmable exit criteria, and wherein the at least one programmable exit criterion is satisfied when each criterion of the plurality of programmable exit criteria is satisfied.

48. The method of claim 43, further comprising the steps of:

determining when the intrinsic atrial rate is greater than or equal to a programmable third threshold rate greater than the second threshold rate; and initiating the fallback response when the intrinsic atrial rate is greater than or equal to the third threshold rate.

49. An implantable pacemaker comprising:

first and second leads coupling the pacemaker to, respectively, an atrial chamber and a ventricular chamber of a heart;

atrial sense circuitry for sensing an intrinsic atrial rate through the first lead;

pulse generating circuitry for generating pacing pulses for delivery to the atrial and ventricular chambers through, respectively, the first and second leads; and a control system, coupled to the atrial sense circuitry and also coupled to the pulse generating circuitry, for pacing the ventricular chambers;

wherein the ventricular chambers are paced at a ventricular pacing rate at least equal to a base rate, and at most equal to a maximum tracking rate (MTR); and wherein the control system is operable to:

determine the intrinsic atrial rate by causing the atrial sense circuitry to sense all atrial events of each cardiac cycle, including atrial events occurring during a total atrial refractory period of each cardiac cycle, and initiate a fallback response when the intrinsic atrial rate exceeds a fallback initiating rate higher than the MTR.

50. The pacemaker of claim 49, wherein when the fallback response is initiated the control system is operable to:

incrementally decrease the ventricular pacing rate by a programmable second fallback step during each cardiac cycle, beginning with the cardiac cycle during which the fallback response was initiated;

end the incremental decrease of the ventricular pacing rate when the ventricular pacing rate is less than or equal to a fallback rate which is lower than the MTR but is greater than or equal to the base rate; and set the ventricular pacing rate equal to the fallback rate when the ventricular pacing rate decreases below the fallback rate.

51. The pacemaker of claim 22, further comprising:

means for incrementally decreasing the ventricular pacing rate by a programmable second fallback step during each cardiac cycle, beginning with the cardiac cycle during which the fallback response is initiated;

second monitoring means for determining when the ventricular pacing rate is less than or equal to a fifth threshold rate which is lower than the second threshold rate and greater than or equal to the first threshold rate;

third selection means responsive to the second monitoring means for ending the incremental decrease of the ventricular pacing rate when the ventricular pacing rate is less than or equal to the fifth threshold rate; and third selection means responsive to the second monitoring means for setting the ventricular pacing rate equal to the fifth threshold rate when the ventricular pacing rate is less than the fifth threshold rate.

52. An implantable pacemaker comprising:

lead means for coupling the pacemaker to, respectively, an atrial chamber and a ventricular chamber of a heart;

atrial sensing means for sensing an intrinsic atrial rate in the atrial chamber of a heart, the atrial sensing means comprising means for sensing atrial events during a total refractory period;

pulse generating means for generating pacing pulses for delivery to the atrial and ventricular chambers at a ventricular pacing rate not less than a first threshold rate and not greater than a second threshold rate;

first testing means for determining when the intrinsic atrial rate is less than or equal to the second threshold rate;

first monitoring means responsive to the first testing means for monitoring the intrinsic atrial rate in accordance with at least one programmable fallback exit criterion when the pacemaker is in the fallback response and the intrinsic atrial rate is less than or equal to the second threshold rate;

second testing means for determining when the at least one fallback exit criterion is met;

second trigger means responsive to the second testing means for exiting the fallback response when the at least one fallback exit criterion is met; and first selection means responsive to the second trigger means for setting the ventricular pacing rate equal to the intrinsic atrial rate when the fallback response is exited.

53. An implantable pacemaker having a plurality of operating modes, comprising:

first and second leads coupling the pacemaker to, respectively, an atrial chamber and a ventricular chamber of a heart;

atrial sense circuitry for sensing an intrinsic atrial rate through the first lead;

pulse generating circuitry for generating pacing pulses for delivery to the atrial and ventricular chambers through, respectively, the first and second leads, wherein the pulse generating circuitry generates pacing pulses for delivery to the ventricular chambers at a ventricular pacing rate not less than a first threshold rate and not greater than a second threshold rate; and a control system, coupled to the atrial sense circuitry and to the pulse generating circuitry, for initiating a fallback response when the intrinsic atrial rate exceeds a third programmable threshold rate higher than the second threshold rate and wherein the control system maintains the operating mode unchanged during the fallback response.

54. The pacemaker of claim 53:

wherein the control system is operable to monitor the intrinsic atrial rate in accordance with at least one programmable fallback exit criterion when the pacemaker is in the fallback response and the intrinsic atrial rate drops below the second threshold rate; and wherein the control system is operable to exit the fallback response and set the ventricular pacing rate equal to the intrinsic atrial rate when the at least one fallback exit criterion is met.

* * * * *